US008961943B2

(12) United States Patent
Schröder et al.

(10) Patent No.: US 8,961,943 B2
(45) Date of Patent: Feb. 24, 2015

(54) O/W-EMULSIFIERS, O/W-EMULSIONS AND METHODS OF MANUFACTURE THEREOF

(71) Applicant: Symrise AG, Holzminden (DE)

(72) Inventors: Bernd Schröder, Holzminden (DE); Rolf Ohrmann, Tostedt (DE); Martina Issleib, Hoisdorf (DE); Edgar Endlein, Wrestedt (DE)

(73) Assignee: Symrise AG, Holzminden (DE)

( * ) Notice: Subject to any disclaimer, the term of this patent is extended or adjusted under 35 U.S.C. 154(b) by 11 days.

(21) Appl. No.: 13/777,341

(22) Filed: Feb. 26, 2013

(65) Prior Publication Data

US 2013/0177510 A1 Jul. 11, 2013

Related U.S. Application Data

(62) Division of application No. 12/678,901, filed as application No. PCT/EP2007/059902 on Sep. 19, 2007, now Pat. No. 8,454,941.

(51) Int. Cl.
| | | |
|---|---|---|
| A61K 6/00 | (2006.01) | |
| A61K 8/18 | (2006.01) | |
| A61Q 17/04 | (2006.01) | |
| A01N 25/00 | (2006.01) | |
| A61K 47/00 | (2006.01) | |
| A61K 8/06 | (2006.01) | |
| A61K 8/24 | (2006.01) | |
| A61K 8/34 | (2006.01) | |
| A61K 8/37 | (2006.01) | |
| A61K 8/55 | (2006.01) | |
| A61Q 19/00 | (2006.01) | |
| B01F 17/00 | (2006.01) | |

(52) U.S. Cl.
CPC . *A61K 8/062* (2013.01); *A61K 8/24* (2013.01); *A61K 8/342* (2013.01); *A61K 8/375* (2013.01); *A61K 8/55* (2013.01); *A61Q 19/00* (2013.01); *B01F 17/0085* (2013.01); *A61Q 17/04* (2013.01)
USPC .............................................. 424/59; 514/786

(58) Field of Classification Search
None
See application file for complete search history.

(56) References Cited

U.S. PATENT DOCUMENTS

| | | | |
|---|---|---|---|
| 5,783,174 | A | 7/1998 | Deckner |
| 6,696,067 | B2 | 2/2004 | Brandt et al. |
| 2006/0171913 | A1 | 8/2006 | Schroder |

FOREIGN PATENT DOCUMENTS

| | | |
|---|---|---|
| DE | 10308565 A1 | 9/2004 |
| DE | 10353030 A1 | 7/2005 |
| EP | 0227012 A1 | 7/1987 |

OTHER PUBLICATIONS

Symrise et al.: "PEG-freier O/W Emulgator aus Kalium Cetylphosphat and Palmglyceriden", Research Disclosure, Mason Publications, Hampshire, GB, vol. 468, No. 115, Apr. 1, 2003 (XP007132557).

*Primary Examiner* — Trevor Love
(74) *Attorney, Agent, or Firm* — Novak Druce Connolly Bove + Quigg LLP

(57) ABSTRACT

O/W-emulsifiers are described, comprising:
(a) 30-50% by weight of hardened palm oil glycerides;
(b) 15-35% by weight of potassium cetyl phosphates;
(c) 20-30% by weight of cetyl alcohol, and
(d) 5-15% by weight of potassium phosphate,
in each case with respect to the total mass of the emulsifier. Further described are corresponding O/W-emulsions, comprising an aqueous phase, an oil phase dispersed in the aqueous phase and between 0.25 and 15% by weight of the above-mentioned O/W-emulsifier. Finally, also described are methods for manufacturing such an O/W-emulsion.

18 Claims, No Drawings

O/W-EMULSIFIERS, O/W-EMULSIONS AND METHODS OF MANUFACTURE THEREOF

CROSS REFERENCE TO RELATED APPLICATIONS

This application is a Divisional of application Ser. No. 12/678,901, filed on Apr. 27, 2010, which is a National Phase filing under 35 U.S.C. §371 of PCT/EP2007/059902 filed on Sep. 19, 2007, the entire contents of which is fully incorporated herein by reference.

The present invention concerns oil-in-water emulsifiers (O/W-emulsifiers), oil-in-water emulsions (O/W-emulsions) and methods of manufacture thereof.

Emulsions are normally formed from two liquid phases, which are not miscible. During manufacture one phase is dispersed in finely distributed form in the other phase. An essential distinction is made between two types of emulsion, namely "water-in-oil" and "oil-in-water" emulsions. With the oil-in-water emulsion (O/W-emulsion) the oil represents the internal phase which is dispersed in the external (water) phase. The characteristics of the corresponding emulsion are essentially determined by the external phase, so that water-in-oil emulsions behave rather like oils and oil-in-water emulsions rather like aqueous solutions.

Emulsions which contain alkyl phosphates, that is to say phosphoric acid esters, with alkyl residues with between 6 and 22 atoms, as anionic emulsifiers are known, for example, from EP 1 264 632.

O/W-emulsions containing monoalkyl phosphate salts such as for example monocetyl phosphate are described in EP 0 227 012.

EP 0 251 249 describes mixtures comprising alkyl-hydroxyalkyl-orthophosphoric acid ester mixtures and co-emulsifiers such as for example cetyl stearyl alcohol.

EP 0 427 411 describes sun protection formulations containing neutralized mono- and/or dialkyl phosphates and a wax component, wherein fully hydrogenated vegetable oils are also mentioned.

Research Disclosure No. 468115 of May 2003; No. 469, pages 641-644 and WO 2004/075868 describe an O/W-emulsifier containing (a) hardened palm oil glycerides and (b) potassium cetyl phosphate, wherein the content as a proportion by weight of potassium cetyl phosphate is at least 40% by weight. A preferred embodiment therein concerns an O/W-emulsifier consisting of:
(a) 30-50% by weight of hardened palm oil glycerides;
(b) 40-50% by weight of potassium cetyl phosphate;
(c) 8-15% by weight of cetyl alcohol;
(d) 4-8% by weight of water and
(e) 0-18% by weight of other additives,
wherein the percentages by weight indicated relate to the total mass of the O/W-emulsifier described there. The O/W-emulsifier described in WO 2004/075868 generally has very good characteristics. In some cases, however, insufficient stability of the emulsions containing an emulsifier in accordance with WO 2004/075868 has been noted, in particular in relation to the long-term stability of such emulsions, and here in particular in relation to their thermal stability, especially when incorporating (in particular water-soluble) sun protection filters.

The object of the present invention was to indicate an improved O/W-emulsifier, in particular one that provides improved stability of the corresponding emulsions, in particular with respect to long-term stability of such emulsions, particularly with regard to thermal stability, especially of emulsions containing water-soluble sun protection filters.

The emulsifiers sought should preferably require only a low usage dose, preferably be universally suitable for the manufacture of emulsions with different viscosities (such as lotions, milks and crèmes), preferably be able to be used in a broad pH-range (of for example pH 3 to 11) and preferably have excellent skin compatibility. These emulsifiers should also preferably be free from polyethylene glycol (PEG).

Further, O/W-emulsions containing O/W-emulsifiers according to the invention and methods for the manufacture thereof should be indicated.

The present invention correspondingly concerns an oil-in-water emulsifier (O/W-emulsifier), which is outstandingly suitable for manufacturing O/W-emulsions with improved stability and also in preferred embodiments is free from polyethylene glycol (PEG).

According to an initial aspect of the present invention the given object is achieved by an O/W-emulsifier comprising:
(a) 30-50% by weight of hardened palm oil glycerides;
(b) 15-35% by weight of potassium cetyl phosphates (potassium monocetyl phosphate; potassium dicetyl phosphate);
(c) 20-30% by weight cetyl alcohol, and
(d) 5-15% by weight potassium phosphates,
wherein the percentages by weight indicated relate to the total mass of the O/W-emulsifier.

Potassium monocetyl phosphate (CAS-No.: 19035-79-1; INCI: Potassium Cetyl Phosphate) can also be referred to as the monopotassium salt of the phosphoric acid monohexadecyl ester. Potassium-monocetyl phosphate is for example commercially available under the name Amphisol® K (DSM).

An emulsifier according to the invention comprises, in addition to (b) potassium cetyl phosphate(s) and (c) cetyl alcohol, as a component (a) hardened palm oil glycerides (INCI: Hydrogenated Palm Glycerides) (mono-, di- and triglycerides of fatty acids, contained in palm oil, thus for example the mono-, di- and triglycerides of oleic acid, palmitic acid, stearic acid, myristic acid, lignoceric acid and palmitoleic acid). Hardened palm oil glycerides are commercially available, for example under the name Monomuls® 60-35C.

The emulsifier according to the invention can be used even at small usage dosages for the manufacture of stable, skin-smoothing O/W-emulsions.

The O/W-emulsifier according to the invention preferably contains no polyethylene glycol (PEG) and/or no other glycol and/or no paraffin and/or no isoparaffin, with particular preference none of these substances.

The O/W-emulsifier according to the invention preferably contains or consists of an O/W-emulsifier according to the invention with:
(a) 35-45% by weight of hardened palm oil glycerides;
(b) 15-35% by weight of potassium cetyl phosphates;
(c) 25-30% by weight of cetyl alcohol;
(d) 5-10% by weight of potassium phosphates;
(e) 0-15% by weight of other materials,
wherein the percentages by weight indicated relate to the total mass of the O/W-emulsifier.

Component (e) preferably contains water, with preference for a water content in the range between 0.25 and 10% by weight, with particular preference for the range between 0.50 and 5.0% by weight, in each case with respect to the total mass of the O/W-emulsifier, that is to say the total mass of components (a) to (e).

An O/W-emulsifier according to the invention contains as component (b) preferably potassium monocetyl phosphate and potassium dicetyl phosphate, preferably in a ratio by weight of the potassium monocetyl phosphate to the potassium dicetyl phosphate of 2.5:1 or greater, preferably in a ratio of weight in the range between 10:1 and 2.5:1, with to greater preference for the range between 6:1 and 3:1, and particular preference for the range between 5:1 and 3.5:1.

An O/W-emulsifier according to the invention contains in and/or as component (d) preferably potassium hydrogen phosphate, wherein the proportion of potassium hydrogen phosphates (total of potassium monohydrogen phosphate and potassium dihydrogen phosphate) is preferably at least 3% by weight, preferably in the range between 4 and 15% by weight, with particular preference for the range between 5 and 10% by weight, in each case with respect to the total mass of the O/W-emulsifier.

An O/W-emulsifier according to the invention is preferably manufactured by mixing the respective components (a) to (d) and if necessary (e). Alternatively, in order to manufacture an emulsifier according to the invention preferably initially phosphoric acid is converted with an excess quantity of cetyl alcohol, wherein primarily a reaction mixture results which contains phosphoric acid monohexadecyl ester, an unconverted quantity of cetyl alcohol and preferably a proportion of phosphoric acid dihexadecyl ester, wherein the ratio of weight of phosphoric acid monohexadecyl ester to phosphoric acid dihexadecyl ester is preferably at least 2.5:1, on this point see above. This reaction mixture then preferably has potassium hydroxide (preferably in the form of potassium hydroxide solution) or potassium carbonate added, so that an emulsifier according to the invention results.

The O/W-emulsifier according to the invention has the following improved characteristics compared with the O/W-emulsifier according to WO 2004/075868:

lower viscosity of a corresponding emulsion at the same usage concentration of the emulsifier;
higher long-term stability of the corresponding emulsions, in particular of emulsions containing water-soluble UV-filters, especially sulfonated UV-filters;
improved thermal stability of the corresponding emulsions, in particular at temperatures in excess of 40° C.: markedly lower streaking, no or only very little tendency towards phase separation; better thermal cycling test stability;
stronger formation of liquid crystalline structures.

A higher fraction of liquid crystalline structures in O/W-emulsions contributes to a higher stability of the emulsions; a higher fraction of liquid crystalline structures also brings about improved skin moisturization.

In order to assess the long-term stability, the thermal stability of the respective emulsions containing the respective emulsifier under test is observed at constant storage temperature over a storage period of at least 2 months and up to 6 months at constant temperature, at each of 5° C., 20° C., 40° C., 45° C., 50° C., in each case in the dark and also at room temperature (approximately 20° C.) in the daylight. The assessment of the stability takes place regularly after 2 weeks, 1 month, 2 months and 3 months as well as if necessary after 6 months.

In order to assess the thermal cycling test stability the respective emulsion is initially stored for 24 hours at −20° C., and then for 24 hours at +40° C. (this represents one cycle), and then again for 24 hours at −20° C. and so on. A total of up to 10 cycles are carried out and during these the number of cycles noted before separation of the respective emulsion is observed, that is to say a disintegration of the emulsion due to phase separation. If an emulsion is rated at "10 cycles" it demonstrates a very good stability in the thermal cycling test.

The O/W-emulsifier according to the invention has in addition to the abovementioned advantages the following improved characteristics in comparison with pure potassium monocetyl phosphate:

better oil solubility at lower temperatures;
brings about in corresponding emulsions a better/more pleasant feeling on the skin;
in emulsions with pigments (such as for example: ZnO, $TiO_2$): easier manufacture of the emulsion (lower shearing forces necessary in the manufacture of the emulsion), greater stability of emulsion-containing pigments;
significantly stronger formation of liquid crystalline structures;
in combination with stearic acid: markedly lower tendency towards particle formation;
in combination with stearic acid: markedly lower tendency towards discoloration in daylight.

The O/W-emulsifiers according to the invention have a varied range of uses, and in particular can be used for highly viscous crèmes, medium viscosity milks and lotions and thin-bodied, sprayable lotions.

The use of the O/W-emulsifiers according to the invention allows a good dispersion of solid matter in the resultant emulsion systems.

When the O/W-emulsifiers according to the invention are used, the distribution capability of the incorporated active substances is consistently increased.

When the O/W-emulsifiers according to the invention are used, formulations (emulsions) can be manufactured using polar and nonpolar oils.

The O/W-emulsifiers according to the invention are compatible with hydrogel formers and hydrocolloids.

Particularly advantageous is a combination of the O/W-emulsifiers according to the invention with UV-filters (UV/A-, UV/B- and broadband filters) (light protection agents). The use of the emulsifiers according to the invention here leads to consistent improvement in the hygrostability of corresponding sun protection products.

The emulsifier according to the invention is preferably formulated with light protection agents. Preferred protection agents are for example organic UV-absorbers from the group comprising 4-aminobenzoic acid and derivatives, salicylic acid derivatives, benzophenone derivatives, dibenzoylmethane derivatives, diphenylacrylates, 3-imidazol-4-yl-acrylic acid and its esters, benzofuran derivatives, benzylidenmalonate derivatives, polymer UV-absorbers (containing one or more silicon organic residues), cinnamic acid derivatives, camphor derivatives, trianilino-s-triazine derivatives, 2-hydroxyphenylbenzotriazole derivatives, 2-phenylbenzimidazole-5-sulfonic acid and its salts, anthranilic acid menthyl esters, benzotriazole derivatives.

Particularly suitable UV-filters here are
p-aminobenzoic acid;
3-(4'-trimethylammonium)-benzylidene-boman-2-one methyl sulfate;
salicylic acid homomethyl ester (Neo-Heliopan®HMS);
2-hydroxy-4-methoxy-benzophenone (Neo Heliopan®BB);
2-phenylbenzimidazolesulfonic acid (Neo Heliopan®Hydro);
terephthalylidene-dibornanesulfonic acid and salts (Mexoryl®SX);
4-tert-butyl-4'-methoxydibenzoylmethane (Neo Heliopan®357);
3-(4'-sulfo)benzylidene-bornan-2-one and salts;
2-ethylhexyl 2-cyano-3,3-diphenylacrylate (Neo Heliopan®303);

N-[(2 and 4)-[2-(oxoborn-3-ylidene)methyl]benzyl]-acrylamide polymer;
p-methoxycinnamic acid 2-ethylhexyl ester (Neo Heliopan® AV);
p-aminobenzoic acid ethyl ester (25 mol) ethoxylated;
p-methoxycinnamic acid isoamyl ester (Neo Heliopan®E1000);
2,4,6-trianilino-(p-carbo-2'-ethylhexyl-r-oxy)-1,3,5-triazine (Uvinal®T150);
phenol, 2-(2H-benzotriazol-2-yl)-4-methyl-6-(2-methyl-3-(1,3,3,3-tetramethyl-1-(trimethylsilyl)-oxy)-disiloxyanyl)-propyl), (Mexoryl®XL);
4,4'-[(6-[4-(1,1-dimethyl)-aminocarbonyl)-phenylamino]-1,3,5-triazine-2,4-diyl)-diimino]-bis-(benzoic acid 2-ethylhexyl ester), (UvasorbHEB);
3-(4'-methylbenzylidene)-d,l-camphor (Neo Heliopan®MBC);
3-benzylidenecamphor;
salicylic acid 2-ethylhexyl ester (Neo-Heliopan®OS);
4-dimethylaminobenzoic acid 2-ethylhexyl ester (Padimate O);
hydroxyl-4-methoxy-benzophenone-5-sulfonic acid and Na salt;
2,2'-methylene-bis-(6-(2H-benzotriazol-2-yl)-4-1,1,3,3-tetramethylbutyl)-phenol), (Tinosorb®M);
phenylene-bis-benzimidazyl-tetrasulfonic acid disodium salt (Neo Heliopan®AP);
2,4-bis-[{(4-(2-ethyl-hexyloxy)-2-hydroxy}-phenyl]-6-(4-methoxyphenyl)-1,3,5-triazine, (Tinosorb®S);
benzylidenemalonate-polysiloxane (Parsol®SLX);
menthyl anthranilate (Neo Heliopan®MA);
2-(4-diethylamino-2-hydroxybenzoyl)-benzoic acid hexyl ester (Uvinul® A Plus);
indanylidene compounds according to DE 100 55 940 (=WO 02/38537).

A particular advantage of emulsions containing emulsifiers according to the invention and water-soluble UV-filters, in particular sulfonated water-soluble UV-filters, is their high long-term stability, which manifests itself in particular in improved thermal stability above all at temperatures in excess of 40° C.; there is only a slight tendency towards streaking, little or only a very weak tendency towards phase separation and a significantly better thermal cycling test stability observed in comparison with corresponding emulsions which contain an O/W-emulsifier in accordance with WO 2004/075868. The stated advantages concern in particular emulsions according to the invention, on this point see below.

The total quantity of all water-soluble UV-filter substances in a preferred emulsion (according to the invention) is preferably in the range between 0.1 and 12.0% by weight, preferably between 0.5 and 8.0% by weight, with respect to the total weight of the emulsion (according to the invention). Here preference is for (mono- or poly-)sulfonated water-soluble UV-filters, which are preferably selected from the group consisting of phenylene-bis-benzimidazyl-tetrasulfonic acid disodium salt or salts thereof and/or the corresponding disulfonic acid or salts thereof and/or 2-phenylbenzimidazole-5-sulfonic acid or salts thereof and/or 2-hydroxy-4-methoxybenzophenone-5-sulfonic acid or salts thereof and/or 4-(2-oxo-3-bornylidenmethyl)-benzol sulfonic acid or salts thereof and/or 2-methyl-5-(2-oxo-3-bornyliden-methyl)-benzol sulfonic acid or salts thereof and/or benzol-1,4-di-(2-oxo-3-bornylidenmethyl)-10-sulfonic acid or salts thereof.

The emulsifier according to the invention can also be incorporated in cosmetic and/or dermatological preparations, containing pigments, preferably fine-particle pigments. These may be organic or inorganic pigments. A preferred organic pigment is 2,2'-methylene-bis-(6-(2H-benzotriazol-2-yl)-4-1,1,3,3-tetramethylbutyl)-phenol), (Tinosorb®M). Suitable inorganic pigments or micropigments with a basis of metal oxides and/or other metal compounds that are barely soluble or insoluble in water are in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxide systems of the corresponding metals and mixtures of such oxides. These pigments are X-ray amorphous or not X-ray amorphous. Particular preference is for fine-particle pigment with a $TiO_2$ and ZnO base.

The O/W-emulsifier according to the invention can also be incorporated in cosmetic and/or dermatological preparations (emulsions), which have a normal composition and are used for cosmetic and/or dermatological light protection, and also for the treatment, care and cleaning of the skin and/or hair and as a make-up product in decorative cosmetics. Accordingly such preparations, depending on their compositions, can for example be used as skin protection crème, cleaning milk, sun protection lotion, nutrient crème, day or night crème, and so on. Thus such preparations (emulsions) can for example take the form of a lotion, milk, crème, hydrodispersion gel, balm, spray, foam, hair shampoo, hair care agent, hair conditioner, roll-on, stick or make-up.

Of particular advantage are the commercial and logistical advantages, since only an emulsifier has to be procured and stored, in order to manufacture lotions and crèmes.

The O/W-emulsifier according to the invention has very good skin compatibility.

A further advantage of the O/W-emulsifier according to the invention is that it can be manufactured in various forms, with preference for powders, pastilles, extrudates and flakes. The pastille form is also the preferred form of manufacture of the O/W-emulsifier according to the invention.

Because of the chemical composition of the O/W-emulsifiers according to the invention their physical and chemical characteristics are to a large extent set, but certain variations are nevertheless possible.

O/W-emulsifiers according to the invention that meet one, more or preferably all of the following conditions have proven to be particularly advantageous:
following dissolution in neutralized water at a concentration of 10% by weight, with respect to the finished solution, the pH is in the range 5.0-6.5;
the saponification value for a saponification time of 1 hour is in the range 125.0 to 155.0 (test method 211);
the acid value when using the solvent system diethyl ether:ethanol:water 1:1:1 (v/v/v) is in the range between 50.0 and 80.0 mg KOH/g (test method 228).

With regard to the cited test methods 211 or 228 we refer to the examples further on.

The melting point of an O/W-emulsifier according to the invention is preferably adjusted such that it is in the range between 75 and 80° C. The adjustment of the melting point is in particular controlled here by the content of cetyl alcohol in the O/W-emulsifier.

The incorporation of an O/W-emulsifier according to the invention in an O/W-emulsion can optionally take place via the aqueous phase or the oil phase.

The given object of the invention is achieved according to a second aspect by an O/W-emulsion, comprising:
an aqueous phase;
an oil phase dispersed in the aqueous phase and 0.25-15% by weight, preferably 1-15% by weight of an O/W-emulsifier according to the invention, wherein the percentage by weight indicated relates to the total mass of the O/W-emulsion.

For stabilizing emulsions here often a proportion of between 0.25 and 0.50% by weight of the O/W-emulsifier according to the invention is often sufficient.

For the manufacture of O/W-emulsions according to the invention, typically usage concentrations of the O/W-emulsifier according to the invention are applied which are in the range between 0.5 and 3.0% by weight.

For medium viscosity lotions (as an example of emulsions according to the invention) here preferably between 0.5 and 4.0% by weight, preferably between 1.0 and 2.0% by weight, of the O/W-emulsifier according to the invention is used.

Ointments and crèmes routinely contain (as further examples of emulsions according to the invention) between 1.0 and 15.0% by weight, preferably between 1.0 and 3.0% by weight of the O/W-emulsifier according to the invention.

In some embodiments it can be an advantage to incorporate the O/W-emulsifier according to the invention in the aqueous phase, and in doing so to simultaneously process an alcohol, preferably a diol or polyol, with it. In this way the temperature at which the O/W-emulsifier according to the invention dissolves in the aqueous phase can be lowered. The O/W-emulsifier according to the invention is in this case preferably pre-dissolved in an alcohol, preferably a diol or polyol, preferably glycerin and/or 1,2-propylene glycol and/or pentylene glycol (1,2-pentane diol). The liquid phase of O/W-emulsifier and alcohol is then preferably subsequently mixed with the other components of the aqueous phase. Alternatively the alcohol(s) can also be incorporated in advance in the aqueous phase, wherein the O/W-emulsifier according to the invention is then added to the resultant aqueous phase.

The O/W-emulsions according to the invention are characterized inter alia by:
- a good viscosity stability;
- a high pH stability or pH-independent stability;
- a good temperature stability;
- a very fine and homogenous emulsion structure with a brilliant surface and
- commercial and logistical advantages, since only one emulsifier has to be procured and stored in order to manufacture lotions and crèmes.

Apart from the aqueous phase, the oil phase dispersed in the aqueous phase and the M-emulsifier, preferred O/W-emulsions also comprise between 0.1 and 10% by weight of a stabilizer and/or between 1 and 10% by weight of a co-emulsifier, wherein the percentage by weight indicated relates to the total mass of the O/W-emulsion.

The pH of an O/W-emulsion according to the invention can vary within wide ranges. Advantageously the pH is set at a value of between 3 and 11, preferably between 4 and 9, more preferably between 4 and 7.

Examples of co-emulsifiers are glycerin monostearate or other glycerin monoesters of fatty acids, stearic acid or other fatty acids (unsaponified or partially saponified), waxes or fatty alcohols.

As stabilizers hydrogel formers such as for example carbomers, acrylate-cross polymers, xanthans, alginates, and so on, can be used.

Preferred O/W-emulsions are free from polyethylene glycol (PEG), other glycols, paraffin and/or isoparaffin. Preferably none of these substances is present.

The O/W-emulsion according to the invention can comprise further components, in particular:
dispersed solids,
and/or
UV-A- and/or UV-B-filters,
and/or
an antioxidant,
and/or
a perfume oil,
and/or
other inactive ingredients.

In the case of combination of the emulsifiers according to the invention in the emulsions according to the invention with light protection filters (UV/A- and/or UV/B-filters), their distribution capability on the skin is improved and a greater water resistance is achieved compared with other emulsions.

The emulsifier according to the invention, in an emulsion according to the invention, on its own or together with other cosmetic inactive ingredients, has the following effect: increasing the sun protection factor of UV-filters (UVA and/or UVB protection); stabilization of UV-filters (improved photostabilization); improvement in the solubility and/or suspension of solid UV-filters; increasing the water resistance of sun protection products; support in the formation of a gel network structure; increasing the effectiveness of active materials, such as, for example antioxidants, preservatives, lighteners (skin lighteners) and tanning agents, perfume oils, chelating agents; increasing the substantivity of active ingredients on the skin and/or the hair; improving the distribution of cosmetic oils (plant oils, mineral oils, emollients), active ingredients, vitamins, perfume oils and essential oils on the skin; supporting a uniform distribution of repellent active ingredients; contribution to an optimum distribution of preservative systems in the aqueous phase; supporting the barrier function of the skin; reduction in the agglomeration rate of inorganic UV-filters (titanium dioxide, zinc oxide) and color pigments; supporting the distribution of aluminum salts in antiperspirant products; compatibility with alcohols, also with ethanol; improved stabilization of emulsions as the main or co-emulsifier.

The emulsions according to the invention are of the oil-in-water (O/W) type or the water-in-oil-in-water (W/O/W) type. The emulsions according to the invention may also in particular be formulated as a pencil, stick, aerosol, spray, foam, impregnation solution e.g. for cosmetic tissues, cleansing agents such as for example soap, syndets, skin care product, cream, lotion, milk, emulsion foam, micromulsion, paste, gel (e.g. hydro- or hydrodispersion gel), balsam, serum, roll-on, pump spray, aerosol (foaming, non-foaming or post-foaming), skin care product, foot care product (including keratolytic agents, deodorants), insect repellent, sunscreen preparation, aftersun preparation, shaving preparation, depilatory product, hair care product such as for example shampoo, 2-in-1 shampoo, anti-dandruff shampoo, baby shampoo, shampoo for dry scalp, shampoo concentrate, conditioner, hair tonic, hair rinse, hair cream, hair smoothing product (defrizzing agent, relaxer), hair strengthener (spray), styling aid (e.g. gel), as a blonding product, hair lightener, hair conditioner, hair mousse, hair toning product, deodorant and/or antiperspirant, aftershave balm, pre- and aftershave lotion, eye care cream, make-up, make-up remover, baby product, bath product, or face mask.

Preferred emulsions according to the invention come in the following forms: sun protection milk, sprayable sun milk, sun protection lotion, sun protection crème, face crème with sun protection, hair gel, hair crème, hair tonic rinse, deodorant stick, deodorant roll-on, sprayable deodorant lotion, care lotion for moist tissues, body lotion, skin care crème, tinted day crème, mascara.

It is, if necessary, possible and advantageous to use such preparations as the basis for pharmaceutical formulations. Preference is in particular for those cosmetic and dermatological preparations which are in the form of a skin care or make-up product.

For their application the cosmetic and dermatological preparations mentioned by way of example are applied in a sufficient quantity to the skin and/or hair in the normal way for cosmetics.

The lipid phase can advantageously be selected from the following group of substances:

mineral oils, mineral waxes;
oils, such as triglycerides of capric or caprylic acid, or also of natural oils such as for example castor oil;
fats, waxes and other natural and synthetic fatty bodies, preferably esters of fatty acids with alcohols with a low C number (<10), for example with isopropanol, propylene glycol or glycerin, or esters of fatty alcohols with alkanoic acids with a low C number (<10) or with fatty acids;
alkyl benzoates;
silicon oils such as dimethylpolysiloxane, diethylpolysiloxane, diphenylpolysiloxane and mixed forms of these.

The lipid phase of the emulsions, oleogels or hydrodispersions or lipodispersions within the meaning of the present publication are advantageously chosen from the group comprising esters of saturated and/or unsaturated, branched and/or unbranched alkane carboxylic acids having a chain length of 3 to 30 C atoms and saturated and/or unsaturated, branched and/or unbranched alcohols having a chain length of 3 to 30 C atoms, from the group comprising esters of aromatic carboxylic acids and saturated and/or unsaturated, branched and/or unbranched alcohols having a chain length of 3 to 30 C atoms. Such ester oils can then advantageously be selected from the group comprising isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethyl hexyl palmitate, ethylhexyl laurate, 2-hexyldecyl stearate, 2-octyldodecyl palmitate, oleyl oleate, oleyl erucate, erucyl oleate and synthetic, semi-synthetic and natural mixtures of such esters, e.g. jojoba oil, 2-ethylhexyl-2-ethylhexanoate (e.g. Dragoxat EH), ethylhexyl isononanoate (e.g. Dragoxate 89), cetearyl 2-ethyl hexanoate, diisopropyl adipate, triisononanoin.

The lipid phase can also advantageously be chosen from the group comprising branched and unbranched hydrocarbons and hydrocarbon waxes, silicone oils, dialkyl ethers, the group comprising saturated or unsaturated, branched or unbranched alcohols, and fatty acid triglycerides, in particular the triglycerol esters of saturated and/or unsaturated, branched and/or unbranched alkane carboxylic acids having a chain length of 8 to 24, in particular 12 to 18 C atoms. The fatty acid triglycerides can advantageously be chosen, for example, from the group comprising synthetic, semi-synthetic and natural oils, e.g. olive oil, sunflower oil, soya bean oil, groundnut oil, rapeseed oil, almond oil, palm oil, coconut oil, palm kernel oil and the like.

Any blends of such oil and wax components can advantageously also be used within the context of the present invention.

Cyclomethicone (octamethyl cyclotetrasiloxane) is advantageously used as the silicone oil to be used. Other silicone oils can also be used to similar advantage, however, for example hexamethyl cyclotrisiloxane, polydimethyl siloxane, poly(methylphenyl siloxane).

Mixtures of cyclomethicone and isotridecyl isononanoate, of cyclomethicone and 2-ethylhexyl isostearate are also particularly advantageous.

The aqueous phase of preparations within the context of this publication optionally advantageously contains water-soluble plant extracts, alcohols, diols or polyols (low alkyl), and ethers thereof, preferably ethanol, isopropanol, propylene glycol, glycerin, ethylene glycol monoethyl or monobutyl ether, propylene glycol monomethyl, monoethyl or monobutyl ether, diethylene glycol monomethyl or monoethyl ether and analogous products, also alcohols (low alkyl), e.g. ethanol, 1,2-propanediol, glycerin and in particular one or more thickeners, which can advantageously be chosen from the group comprising silicon dioxide, aluminum silicates, polysaccharides or derivatives thereof, e.g. hyaluronic acid, xanthan gum, hydroxypropyl methyl cellulose, particularly advantageously from the group of polyacrylates, preferably a polyacrylate from the group of so-called carbopols, for example type 980, 981, 1382, 2984, 5984 carbopols, either individually or in combination.

The cosmetic and dermatological preparations (emulsions) within the context of this text can contain cosmetic auxiliary substances, such as are conventionally used in such preparations, e.g. preservatives, antioxidants, vitamins, bactericides, perfumes, substances to prevent foaming, dyes, pigments which have a coloring effect, thickeners, surfactants, emollients, emulsifiers, wetting and/or moisture-retaining substances, moisturizers, fats, oils, waxes, plant extracts or other conventional components of a cosmetic or dermatological formulation such as alcohols, low alkyl alcohols, polyols, low alkyl polyols, polymers, foam stabilizers, complexing agents, electrolytes, organic solvents, propellant gases, silicones or silicone derivatives.

The amounts of cosmetic or dermatological auxiliary substances and carriers and perfume to be used in each case can easily be determined by the person skilled in the art, depending on the nature of the particular product.

An additional content of antioxidants is generally preferred. All antioxidants which are suitable or commonly used for cosmetic and/or dermatological applications can be used as favorable antioxidants.

The amount of antioxidants (one or more compounds) in the preparations is preferably between 0.001 and 30% by weight, particularly preferably between 0.05 and 20% by weight, in particular between 1 and 10% by weight, relative to the total weight of the preparation.

The antioxidants are advantageously chosen from the following group: amino acids (e.g. glycine, histidine, 3,4-dihydroxyphenylalanine, tyrosine, tryptophan) and derivatives thereof, imidazoles (e.g. urocanic acid) and derivatives thereof, peptides (D,L-carnosine, D-carnosine, L-carnosine, anserine) and derivatives thereof, carotenoids, carotenes (e.g. alpha-carotene, beta-carotene, lycopene) and derivatives thereof, chlorogenic acid and derivatives thereof, lipoic acid and derivatives thereof, aurothioglucose, propyl thiouracil and other thiols (e.g. thioredoxine, glutathione, cysteine, cystine, cystamine and glycosyl derivatives and N-acyl derivatives thereof or alkyl esters thereof) and salts thereof, dilauryl thiodipropionate, distearyl thiodipropionate, thiodipropionic acid and derivatives thereof and phenolic acid amides of phenolic benzylamines (e.g. homovanillic acid, 3,4-dihydroxyphenylacetic acid, ferulic acid, sinapic acid, caffeic acid, dihydroferulic acid, dihydrocaffeic acid, vanillomandelic acid or 3,4-dihydroxymandelic acid amides of 3,4-dihydroxybenzylamine, 2,3,4-trihydroxybenzylamine or 3,4,5-trihydroxybenzylamine), catechol oximes or catechol oxime ethers (e.g. 3,4-dihydroxybenzaldoxime or 3,4-dihydroxybenzaldehyde-O-ethyloxime), 2-hydrazino-1,3-thiazoles and derivatives, also (metal) chelators (e.g. 2-hydroxy fatty acids, phytic acid, lactoferrin), humic acid, bile acids, bile extracts, bilirubin, biliverdin, folic acid and derivatives thereof, ubiquinone and ubiquinol and derivatives thereof, vitamin C and derivatives thereof (e.g. ascorbyl palmitate, magnesium ascorbyl phosphate, ascorbyl acetate), tocopherols and derivatives (e.g. vitamin E acetate), vitamin A and derivatives (e.g. vitamin A palmitate), rutinic acid and derivatives thereof, flavonoids (e.g. quercetin, alpha-glycosyl rutin) and derivatives thereof, phenolic acids (e.g. gallic acid, ferulic acid) and derivatives thereof (e.g. gallic acid propyl ester, gallic acid ethyl ester, gallic acid octyl ester), furfurylidene glucitol, dibutyl hydroxytoluene, butyl hydroxyanisole, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, resveratrol).

Likewise advantageous antioxidants are described in EP 0 900 781, EP 1 029 849, EP 1 066 821, WO 01/43712, WO 01/70176, WO 01/98235 or also in WO 01/98258.

If vitamin E and/or derivatives thereof are used as the antioxidant(s), it is advantageous to choose their concentrations from the range between 0.001 and 10% by weight, relative to the total weight of the formulation.

If vitamin A or vitamin A derivatives or carotenes or derivatives thereof are used as the antioxidant(s), it is advantageous to choose their concentrations from the range between 0.001 and 10% by weight, relative to the total weight of the formulation.

Other preferred embodiments of the invention result from the attached claims.

The invention is explained in more detail in the following using examples. Unless otherwise stated, all data relate to the weight.

EXAMPLE 1

Emulsifiers According to the Invention

| Component | Example 1A (% by weight) | Example 1B (% by weight) |
|---|---|---|
| Hardened palm oil glycerides | 39.8 | 40.0 |
| Potassium monocetyl phosphate | 23.5 | 14.8 |
| Potassium dicetyl phosphate | 4.5 | 3.6 |
| Cetyl alcohol | 25.5 | 29.5 |
| Potassium phosphate | 5.5 | 8.9 |
| Water | 0.55 | 0.7 |
| Other | To 100 | To 100 |

EXAMPLE 2

Emulsifier for Comparison According to WO 2004/075868 (Not According to the Invention)

| Component | % by weight |
|---|---|
| Hardened palm oil glycerides | 40.0 |
| Potassium mono cetyl phosphate | 40.0 |
| Cetyl alcohol | 15.0 |
| Water | 5.0 |

EXAMPLE 3

Stability Test of Emulsions I-IV in Comparison

|   | Starting material | INCI | I | II | III | IV |
|---|---|---|---|---|---|---|
| A | Emulsifier according to Example 1A | | 1.0 | | | |
|   | Emulsifier according to Example 1B | | | 0.5 | | |
|   | Emulsifier according to Example 2; WO 2004/075868 | Potassium Cetyl Phosphate, Hydrogenated Palm Glyceride | | | 1.0 | 0.5 |
|   | Finsolv TN | C12-15 Alkyl Benzoate | 5.0 | 5.0 | 5.0 | 5.0 |
|   | Copherol 1250 | Tocopheryl Acetate | 0.5 | 0.5 | 0.5 | 0.5 |
|   | Lanette O | Cetearyl Alcohol | 1.0 | 1.0 | 1.0 | 1.0 |
|   | Neutral oil | Caprylic/Capric Triglyceride | 2.0 | 2.0 | 2.0 | 2.0 |
|   | Dow Corning 246 Fluid | Cyclohexasiloxane | 2.0 | 2.0 | 2.0 | 2.0 |
|   | Neo Heliopan ® 357 | Butyl Methoxydibenzoylmethane | 1.0 | 1.0 | 1.0 | 1.0 |
|   | Neo Heliopan ® OS | Ethylhexyl Salicylate | 5.0 | 5.0 | 5.0 | 5.0 |
|   | Neo Heliopan ® AV | Ethylhexyl Methoxycinnamate | 3.0 | 3.0 | 3.0 | 3.0 |
|   | Neo Heliopan ® MBC | 4-Methylbenzoylidene Camphor | 1.5 | 1.5 | 1.5 | 1.5 |
|   | EDTA BD | Disodium EDTA | 0.1 | 0.1 | 0.1 | 0.1 |
|   | Keltrol T | Xanthan Gum | 0.2 | 0.2 | 0.2 | 0.2 |
|   | Carbopol EDT 2050 | Carbomer | 0.2 | 0.2 | 0.2 | 0.2 |
| B | Water, demin. | Water (Aqua) | 59.9 | 60.4 | 59.9 | 60.4 |
|   | Glycerin | Glycerin | 4.7 | 4.7 | 4.7 | 4.7 |
|   | Dragocid Liquid | Phenoxyethanol Methylparaben, Ethylparaben | 0.7 | 0.7 | 0.7 | 0.7 |

-continued

| Starting material | INCI | I | II | III | IV |
|---|---|---|---|---|---|
| Neo Heliopan ® AP, 22% solution neutralized with TEA | Butylparaben, Propylparaben, Isobutylparaben Disodium Phenyl Dibenzimidazole Tetrasulfonate | 4.55 | 4.55 | 4.55 | 4.55 |
| Neo Heliopan ® Hydro 30% solution neutralized with TEA | Phenylbenzimidazole Sulfonic Acid | 6.67 | 6.67 | 6.67 | 6.67 |
| C Triethanolamine | Triethanolamine | 0.5 | 0.5 | 0.5 | 0.5 |
| D Perfume oil | Fragrance | 0.4 | 0.4 | 0.4 | 0.4 |
| Alpha-Bisabolol nat. | Bisabolol | 0.1 | 0.1 | 0.1 | 0.1 |
| Data in % by weight | Total: | 100 | 100 | 100 | 100 |

TEA: Triethanolamine

The pH of emulsions I-IV was stable throughout the period of observation (3 months) at between 7.7 and 7.8.

Manufacturing Specification:

Heat phases A and B to approximately 80° C., disperse the gel formers (xanthan gum, carbomer) in A, add phase B to A and homogenize, in doing so add part C, stir cold, then add part D at 40-35° C.

Assessment of Long-Term Stability:

| Temperature | Duration/Period | I | II | III | IV |
|---|---|---|---|---|---|
| 5° C. | 3 months | A | A | S1 | S2 |
| 40° C. | 2 months | S0 | S0 | S1 | S2 |
| 40° C. | 3 months | S0 | S0 | S2 | S3 |
| 50° C. | 1 month | A | A | S1 | S1 |
| 50° C. | 2 months | S0 | S0 | S3 | S3 |
| 50° C. | 3 months | S1 | S1 | S3 | P1 |

Assessment:
A = good stability, no significant change;
S0 = slight streaking, but still acceptable;
S1 = slight streaking;
S2 = clear streaking;
S3 = heavy streaking;
P1 = phase separation.

Thermal Cycling Test (1 Cycle=24 Hours at −20° C., then 24 Hours at +40° C.):

| I | II | III | IV |
|---|---|---|---|
| 10 cycles | 10 cycles | 10 cycles | 8 cycles |

The emulsions not according to the invention III and in particular IV exhibited a significantly poorer long-term stability.

EXAMPLE 4

Stability Test of Emulsions V and VI in Comparison

| | Starting material | INCI | V | VI |
|---|---|---|---|---|
| A | Emulsifier according to Example 1A | | 0.50 | — |
| | Emulsifier according to Example 2; | | — | 0.50 |

-continued

| | Starting material | INCI | V | VI |
|---|---|---|---|---|
| | WO 2004/075868 Dracorin GMS | Glyceryl Stearate | 0.50 | 0.50 |
| | Paraffin oil | Paraffinum Liquidum | 25.00 | 25.00 |
| | Abil 350 | Dimethicone | 2.00 | 2.00 |
| | Carbopol Ultrez 10 | Carbomer | 0.10 | 0.10 |
| | Keltrol RD | Xanthan Gum | 0.10 | 0.10 |
| B | Demineralized water | Water (Aqua) | 70.45 | 70.45 |
| | Dragocid liquid | Phenoxyethanol, Methylparaben, Ethylparaben, Butylparaben, Propylparaben, Isobutylparaben | 0.80 | 0.80 |
| C | NaOH, 10% aqueous solution | Sodium Hydroxide | 0.25 | 0.25 |
| D | Parfum | Fragrance (Parfum) | 0.30 | 0.30 |
| | Total | | 100.0 | 100.0 |
| | pH | | 6.2 | 6.3 |

Manufacturing Specification:

Weigh-in phase A excluding carbomer, xanthan gum, heat to 80° C., then add carbomer, xanthan gum and homogenize. Heat phase B to approximately 80° C., add B to A and homogenize, in doing so add part C. Stir cold, at 40-35° C. add part D.

The pH of emulsions V and VI was stable throughout the period of observation (3 months).

Assessment of Long-Term Stability:

| Temperature | Duration/Period | V | VI |
|---|---|---|---|
| 40° C. | 1 month | A | S1 |
| 40° C. | 2 months | S0 | S2 |
| 50° C. | 2 weeks | A | V1 |
| 50° C. | 1 month | S0 | S1 |
| 50° C. | 2 months | S1 | S3 |
| 50° C. | 3 months | S1 | P1 |

Assessment:
A = good stability, no significant change;
V1 = slight decrease in viscosity;
S0 = slight streaking, but still acceptable;
S1 = slight streaking;
S2 = clear streaking;
S3 = heavy streaking;
P1 = phase separation.

Thermal Cycling Test (1 Cycle=24 Hours at −20° C., then 24 Hours at +40° C.):

| V | VI |
|---|---|
| 10 cycles | 4 cycles |

The emulsion VI not according to the invention exhibited a significantly poorer long-term stability.

FORMULATION EXAMPLES

Example F1

Sun Protection Milk (O/W)

Example F2

Sun Protection Lotion (O/W)

Example F3

Face Crème (O/W) with Sun Protection

Example F4

Sun Protection Milk

| | Starting material | INCI Name | F1 | F2 | F3 | F4 |
|---|---|---|---|---|---|---|
| A | Abil 100 | Dimethicone | 0.3 | | 0.3 | |
| | Cetiol OE | Dicaprylyl Ether | 5.0 | 5.0 | 1.5 | |
| | Copherol 1250 | Tocopheryl Acetate | 0.5 | 0.5 | 0.5 | 0.5 |
| | Corapan TQ ® | Diethylhexyl 2,6-naphthalate | 2.0 | 5.0 | 5.0 | 2.5 |
| | Cutina FS 45 | Palmitic Acid (and) Stearic Acid | | 2.0 | | |
| | Cutina MD | Glyceryl Stearate | 2.0 | 1.0 | 2.0 | |
| | Dragoxat 89 | Ethylhexyl Isononanoate | | | 1.5 | |
| | Edeta BD | Disodium EDTA | | | | 0.1 |
| | Emulsifier according to Example 1A | | 1.5 | 0.3 | | |
| | Emulsifier according to Example 1B | | | | 1.5 | 0.5 |
| | Hostacerin DGMS | Polyglyceryl-2 Stearate | | | | 4.0 |
| | Keltrol T | Xanthan Gum | | | | 0.4 |
| | Lanette 16 | Cetyl Alcohol | 1.2 | | 1.5 | |
| | Lanette O | Cetearyl Alcohol | | 1.0 | | |
| | Miglyol 812 | Caprylic/Capric Triglyceride | | | | 5.0 |
| | Neo Heliopan ® 357 | Butyl Methoxydibenzoylmethane | 1.0 | 0.8 | 2.0 | 1.5 |
| | Neo Heliopan ® HMS | Homosalate | 7.0 | | 5.0 | 8.0 |
| | Neo Heliopan ® MBC | 4-Methylbenzylidene Camphor | | 3.0 | | |
| | Neo Heliopan ® OS | Ethylhexyl Salicylate | | | 5.0 | |
| | PCL Liquid | Cetearyl 2-Ethylhexanoate | 4.0 | 5.0 | | |
| | Prisorine 3505 | Isostearic Acid | | | | 0.5 |
| | SF 1214 | Cyclopentasiloxane (and) Dimethicone | | | | 1.0 |
| | Solbrol P | Propylparaben | 0.1 | 0.1 | 0.1 | 0.1 |
| | Tegosoft TN | C12-15 Alkyl Benzoate | | | | 4.0 |
| | Trilon BD | EDTA | | | 0.1 | |
| | Zinc oxide, neutral | Zinc Oxide | | | | 7.0 |
| B | 1,3-Butylene glycol | Butylene Glycol | 3.0 | 3.0 | | |
| | Carbopol ETD 2050 | Carbomer | 0.2 | 0.2 | 0.3 | |
| | Glycerin | Glycerin | | | 3.0 | 4.0 |
| | Keltrol T | Xanthan Gum | 0.2 | 0.2 | 0.5 | |
| | Lanette E | Sodium Cetearyl Sulfate | | | | 0.75 |
| | Sodium hydroxide solution, 10% aq. | Sodium Hydroxide | | | | 2.5 |
| | Neo Heliopan ® AP | Disodium Phenyl Dibenzimidazole Tetrasulfonate | 22.0 | 22.0 | 25.0 | 2.2 |
| | Neo Heliopan ® AP, 10% solution Neutralized with NaOH | Disodium Phenyl Dibenzimidazole Tetrasulfonate | | | | |
| | Phenoxyethanol | Phenoxyethanol | 0.7 | 0.7 | 0.7 | 0.7 |
| | Solbrol M | Methylparaben | 0.2 | 0.2 | 0.2 | 0.2 |
| | Water, distilled | Water (Aqua) | 45.9 | 47.2 | 40.4 | 54.05 |
| C | Sodium hydroxide solution, 10% aq. | Sodium Hydroxide | 2.8 | 2.4 | 3.5 | |
| | Perfume oil | Fragrance (Parfum) | | | | 0.5 |
| D | Perfume oil | Fragrance (Parfum) | 0.3 | 0.3 | 0.3 | |
| | -(-Alpha-)-Bisabolol nat. | Bisabolol | 0.1 | 0.1 | 0.1 | |
| | Data in % by weight | Total: | 100 | 100 | 100 | 100 |

Manufacturing Specifications:

Examples F1/F2/F3: in each case part A: heat to approximately 85° C. Part B: weigh-in starting materials excluding Carbopol and Keltrol. Disperse Carbopol and Keltrol with Ultra Turrax. Heat to approximately 85° C. Add part B to A. Part C: add immediately to NB and then homogenize hot (Ultra Turrax). Allow to cool while stirring. Part D: add and stir.

Example F4: Part A: heat to approximately 85° C. (excluding Keltrol and zinc oxide). Disperse Keltrol and zinc oxide with the Ultra Turrax in the hot lipid phase. Part B: heat to approximately 85° C. Add B to A. Cool to 60° C. while stirring and homogenize (Ultra Turrax). Then allow to cool to room temperature (approximately 20° C.) while stirring. Part C: add and homogenize.

Examples F1-F4 should be understood to be standard formulations, since other sun filters (alone or as sun filter compositions) can equally profit from a combination of the emulsifiers according to the invention.

Example F5

Hair Gel-Wax for Men

Example F6

Hair Crème (O/W)

Example F7

Hair Rinse (O/W)

Example F8

Sensitive Balsam Roll-on (O/W)

Example F9

Skincare Lotion with Moisturizer (O/W)

Example F10

Skincare Crème (O/W)

| | Starting material | INCI Name | F5 | F6 | F7 | F8 | F9 | F10 |
|---|---|---|---|---|---|---|---|---|
| A | Abil 350 | Dimethicone | | | | | | 1.5 |
| | Abil B 8852 | Dimethicone Copolyol | | 1.0 | | | | |
| | Cetiol HE | PEG-7 Glyceryl Cocoate | 1.0 | | | | | |
| | Cutina HR Plv. | Hydrogenated Castor Oil | | | 0.5 | | | |
| | Dracorin GMS | Glyceryl Stearate | | | 3.0 | 2.0 | | 1.0 |
| | Drago-Oat-Active | Water (Aqua), Butylene Glycol, *Avena Sativa* (Oat) Kernel Extr. | | | | | 1.0 | |
| | Dragoxat 89 | Ethylhexyl Isononanoate | | | | | | 7.0 |
| | Emulsifier according to Example 1A | | 15.0 | | 1.0 | | | |
| | Emulsifier according to Example 1B | | | | | | 0.5 | 2.0 |
| | Eumulgin B2 | Ceteareth-20 | | | | 2.0 | | |
| | Farnesol | Farnesol | | 0.1 | | | | |
| | Fitoderm | Vegetable Squalane | | | | | | 3.0 |
| | Lanette 16 | Cetyl Alcohol | | | | 2.5 | | 4.0 |
| | Lanette 0 | Cetearyl Alcohol | 15.0 | 4.0 | 1.5 | | | |
| | Solubilizer | PEG-40 Hydrogenated Castor Oil, Trideceth-9, Water (Aqua) | | | | | | |
| | Neo-Dragocid liquid | Triethylene Glycol, Imidazolidinyl Urea, Methylparaben, Propylparaben, Dehydroacetic Acid | | | | | 0.4 | |
| | Neutral oil | Caprylic/Capric Triglyceride | 10.0 | | | | | |
| | PCL Liquid 100 | Cetearyl Ethylhexanoate | 5.0 | 2.0 | 0.5 | 1.0 | | |
| | Pemulen TR-2 | Acrylates/C10-30 Alkyl Acrylate Crosspolymer | | | | | 0.2 | |
| | Rewoderm LI 520-70 | PEG-200 Hydrogenated Glyceryl Palmate | 1.5 | | | | | |
| | Varisoft BT 85 | Behentrimonium Chloride | | | 1.0 | | | |
| | Varisoft TA 100 | Distearyldimonium Chloride | | | | 2.0 | | |
| | Water | Water (Aqua) | | | | | 76.6 | |
| B | -(-Alpha-)Bisabolol, nat. | Bisabolol | | | | | 0.1 | |
| | Aloe Vera-Gel-conc. 10/1 | Water (Aqua), *Aloe Barbadensis* Gel | | | | | 1.0 | |
| | Butylene glycol | Butylene Glycol | 1.0 | | | | | |
| | Citric acid, 10% in water | Citric Acid | 0.3 | | | | | |
| | Dragocid Liquid | Phenoxyethanol, Methylparaben, Ethylparaben, Butylparaben, Propylparaben, Isobutylparaben | | | | 0.8 | 0.8 | 0.8 |

-continued

| Starting material | INCI Name | F5 | F6 | F7 | F8 | F9 | F10 |
|---|---|---|---|---|---|---|---|
| Dragoxat 89 | Ethylhexyl Isononanoate | | | | | 8.0 | |
| Emulsifier according to example 1A | | | | | | 0.8 | |
| Emulsifier according to example 1B | | | | 2.0 | | | |
| Glycerin | Glycerin | | 6.0 | | | | 3.0 |
| Glydant Plus Liquid | DMDM Hydantoin, Iodopropynyl Butylcarbamate | 0.2 | | | | | |
| Keltrol F | Xanthan Gum | | | | | | 0.25 |
| Paraffin oil 5 Grade E | Paraffinum Liquidum | | | | | 8.3 | |
| PCL Liquid 100 | | | | | | 3.9 | |
| Water | | 50.8 | 82.7 | 86.7 | 88.2 | | 77.15 |
| C Deolite | Pentylene Glycol, Dimethyl Phenylpropanol | | | | 1.0 | | |
| Dragocid Liquid | Phenoxyethanol, Methylparaben, Ethylparaben, Butylparaben, Propylparaben, Isobutylparaben | | | 0.8 | | | |
| Dragoderm | Glycerin, *Triticum Vulgare* (Wheat) Gluten, Water Aqua | | | | 3.5 | | |
| NaOH 10% solution | Sodium Hydroxide | | | | | 0.4 | |
| Perfume oil | Fragrance | 0.2 | 0.4 | 0.5 | 1.0 | | |
| D Perfume oil | Fragrance | | | | | 0.3 | 0.3 |
| Data in % by weight | Total: | 100 | 100 | 100 | 100 | 100 | 100 |

Manufacturing Instructions:

Example F5: Heat A and B separately from one another to 75° C. Combine under moderate stirring until the gel-wax is homogenous. Then allow to cool, add phase C at approximately 40° C. and stir until homogenous. pH: approximately 5.2.

Example F6: mix all starting materials in Phase A, heat to 80° C. and homogenize with an Ultra Turrax. Stir cold with a blade agitator, reducing the speed of stirring as the temperature drops. Add Phase C at approximately 35° C. pH: approximately 5.9.

Examples F7/F8: Heat each of Phases A and B separately from one another to approximately 80° C. Add Phase B to A (Ultra-Turrax) and emulsify. Stir cold with a blade agitator, reducing the speed of stirring as the temperature drops. Add Phase C at approximately 30° C. pH: approximately 4.2 for (F7) and 5.2 for (F8).

Examples F9/F10: In each case swell the Pemulen TR-2 or Keltrol F in water using an Ultra-Turrax. Heat phases A and B separately from one another, to approximately 80° C. Add Phase B to A (Ultra-Turrax) and emulsify. Add Phase C and homogenize again. Stir cold with a blade agitator, reducing the speed of stirring as the temperature drops. Add Phase D at approximately 35° C. pH: approximately 5.5 for (F9) and 5.2 for (F10).

The above Examples F7, F8 and F9 are formulation examples for low viscosity and sprayable emulsions. A further formulation example for a low viscosity, that is to say sprayable, formulation is provided by the following Example 11.

Example F11

Sprayable Sun Milk

| Starting materials | INCI Name | % by weight | % by weight |
|---|---|---|---|
| Phase A | | | |
| Water | Water (Aqua) | 73.60 | 73.60 |
| Pemulen TR-2 | Acrylates/C10-30 Alkyl Acrylate Crosspolymer | 0.20 | 0.20 |
| Neo-Dragocid fluid | Triethylen Glycol, Imidazolidinyl Urea, Methylparaben, Propylparaben, Dehydroacetic Acid | 0.40 | 0.40 |
| Drago-Oat-Active | Water (Aqua), Butylene Glycol, *Avena Sativa* (Oat) Kernel Extract | 1.00 | 1.00 |
| Phase B | | | |
| Emulsifier according to Example 1A | | 0.80 | |

-continued

| Starting materials | INCI Name | % by weight | % by weight |
|---|---|---|---|
| Emulsifier according to Example 1B | | | 0.80 |
| Dragoxat 89 | Ethylhexyl Isononanoate | 8.00 | 8.00 |
| Paraffin oil 5 Grade E | Paraffinum Liquidum | 8.30 | 8.30 |
| -(-Alpha-)Bisabolol, natural | Bisabolol | 0.10 | 0.10 |
| Neo Heliopan A V | Ethylhexyl Methoxy-cinnamate | 3.00 | 3.00 |
| Neo Heliopan MBC | 4-Methylbenzylidene Camphor | 3.00 | 3.00 |
| Neo Heliopan 357 | Butyl Methoxybenzoyl-methane | 0.90 | 0.90 |
| Phase C | | | |
| Sodium hydroxide 10% solution | Sodium Hydroxide | 0.40 | 0.40 |
| Phase D | | | |
| Perfume oil | Fragrance | 0.30 | 0.30 |

Formulation examples for high viscosity and very hard emulsions are provided by the following Examples F12 and F13

Example F12

Sun Protection Crème (O/W)

| Starting materials | INCI Name | % by weight | % by weight |
|---|---|---|---|
| Phase A | | | |
| Emulsifier according to Example 1A | | 2.00 | |
| Emulsifier according to Example 1B | | | 2.00 |
| Lanette O | Cetearyl Alcohol | 1.00 | 1.00 |
| Edenor L2 S.M. | Stearic Acid, Palmitic Acid | 4.00 | 4.00 |
| Neutral oil | Caprylic/Capric Acid | 10.00 | 10.00 |
| Dow Corning 200 Fluid 100 cS | Dimethicone | 0.30 | 0.30 |
| Neo Heliopan AV | Ethylhexyl Methoxycinnamate | 7.50 | 7.50 |
| Neo Heliopan BB | Benzophenone-3 | 4.50 | 4.50 |
| Neo Heliopan 357 | Butyl Methoxydibenzoylmethane | 2.00 | 2.00 |
| Phase B | | | |
| Water | Water (Aqua) | 66.86 | 66.86 |
| Carbopol 980 | Carbomer | 0.40 | 0.40 |
| Potassium hydroxide 50% aqueous solution | Potassium Hydroxide | 0.34 | 0.34 |
| Dragocid Liquid | Phenoxyethanol, Methylparaben, Ethylparaben, Butylparaben, Propylparaben, Isobutylparaben | 0.80 | 0.80 |
| Phase C | | | |
| Perfume oil | Fragrance | 0.30 | 0.30 |

Example F13

Skincare Crème (O/W)

| Starting materials | INCI Name | % by weight | % by weight |
|---|---|---|---|
| Phase A | | | |
| Emulsifier according to Example 1A | | 2.00 | |
| Emulsifier according to Example 1B | | | 2.00 |
| Dragoxat 89 | Ethylhexyl Isononanoate | 7.00 | 7.00 |
| Lanette 16 | Cetyl Alcohol | 4.00 | 4.00 |
| Dracorin GMS | Glyceryl Stearate | 1.00 | 1.00 |
| Fitoderm | Vegetable Squalane | 3.00 | 3.00 |
| Abtil 350 | Dimethicone | 1.50 | 1.50 |
| Phase B | | | |
| Water | Water (Aqua) | 77.15 | 77.15 |
| Keltrol F | Xanthan Gum | 0.25 | 0.25 |
| Dragocid Liquid | Phenoxyethanol, Methylparaben, Ethylparaben, Butylparaben, Propylparaben, Isobutylparaben | 0.80 | 0.80 |
| Glycerin 85% in water | Glycerin | 3.00 | 3.00 |
| Phase C | | | |
| Perfume oil | Fragrance | 0.30 | 0.30 |

Example F14

Sun Protection Milk with High Sun Protection Factor

| Starting materials | INCI Name | % by weight | % by weight |
|---|---|---|---|
| Phase A | | | |
| Emulsifier according to Example 1A | | 2.00 | |
| Emulsifier according to Example 1B | | | 2.20 |
| Parsol ® SLX | Poylsilicone-15 | 6.00 | 6.00 |
| Neo Heliopan ® 357 | Butyl Methoxydibenzoylmethan | 2.00 | 2.00 |
| Parsol ® 5000 | 4-Methylbenzylidene Camphor | 4.00 | 4.00 |
| Uvinul ® T150 | Ethylhexyltriazone | 2.00 | 2.00 |
| Silicone DC 200/350 cs | Dimethicone | 1.00 | 1.00 |
| Lanette O | Cetearyl Alcohol | 2.00 | 2.00 |
| Softisan 100 | Hydrogenated Coco-Glycerides | 3.00 | 3.00 |
| Tegosoft TN | C12-15 Alkyl Benzoate | 6.00 | 6.00 |
| Cetiol B | Dibutyl Adipate | 7.00 | 7.00 |
| Vitamin E acetate | Tocopheryl Acetate | 2.00 | 2.00 |
| BHT | BHT | 0.05 | 0.05 |
| Edeta BD | Disodium EDTA | 0.10 | 0.10 |
| Phenonip | Phenoxyethanol, Methylparaben, Ethylparaben, Propylparaben Butylparaben | 0.60 | 0.60 |

-continued

| Starting materials | INCI Name | % by weight | % by weight |
|---|---|---|---|
| Phase B | | | |
| Water | Water (Aqua) | To 100 | To 100 |
| 1,2-Propylene glycol | Propylene Glycol | 5.00 | 5.00 |
| Carbopol 980 | Carbomer | 0.30 | 0.30 |
| KOH, 10% aqueous solution | Potassium Hydroxide | 1.50 | 1.50 |
| Phase C | | | |
| Encapsulated UV-Filter Eusolex ® UV-Pearls ™ OMC | Ethylhexyl Methoxycinnamate | 12.00 | 18.00 |
| Phase D | | | |
| Perfume oil | Fragrance | 0.30 | 0.30 |

Test Method 211 to Determine the Saponification Number

Approximately 1.5 g of the sample are accurately weighed and have 25.00 ml 0.5 N ethanolic sodium hydroxide solution added. Following addition of a boiling stone, the mixture is held at boiling point for 1 hour with reflux cooling. Then the excess lye is titrated into the still warm mixture following the addition of a few drops of a 0.1% ethanolic thymolphthaleine solution at 40° C. with the most intensive stirring with 0.5 N sulfuric acid until the indicator changes color. After the further addition of a little thymolphthaleine solution, stirring takes place for a further 2 minutes at 40° C. The possibly once more colored liquid is again titrated with 0.5 N sulfuric acid until discoloration.

In the same way a blank test is to be started. From the difference between the 0.5 N sulfuric acid used in the blank test and the main test the saponification number is calculated.
Calculation:

$$\text{Acid value} = \frac{(B-H) * 28}{w}$$

B=milliliters of 0.5 N sulfuric acid used in the blank test
H=milliliters of 0.5 N sulfuric acid used in the main test
w=weighed-in amount of substance in the sample in grams.
Test Method 228 for Determination of the Acid Value Approximately 2.5 g of the substance under test are weighed into a 300 ml wide-necked conical flask, 50 ml of a mixture of the same proportions by volume of diethyl ether/ethanol/water (neutralized against phenolphthalein) are added and under gentle heating on the water bath (max. 35° C.) extensively brought into solution. The conical flask is covered here with a watch-glass. Full dissolution of the substance does not take place here; the result is simply a cloudy dispersion. Immediately after dissolution, titration takes place with a 0.1 N KOH solution until the first appearance of a weak pink discoloration.
Calculation:

$$\text{Acid number} = \frac{a * 5.61}{w}$$

a=number of milliliters used of 0.1 N potassium hydroxide solution
w=weighed-in substance in grams

The invention claimed is:

1. An O/W-emulsion comprising:
    an aqueous phase;
    an oil phase dispersed in the aqueous phase; and
    0.25-15% by weight of an O/W-emulsifier, wherein the percentage by weight indicated relates to the total mass of the O/W-emulsion; and wherein the O/W-emulsifier comprises:
    (a) 30-50% by weight of hardened palm oil glycerides;
    (b) 15-35% by weight of potassium cetyl phosphates;
    (c) 20-30% by weight of cetyl alcohol; and
    (d) 5-15% by weight of potassium phosphates; wherein the percentages by weight for components (a)-(d) relate to the total mass of the O/W-emulsifier, and wherein the potassium phosphates of component (d) do not comprise cetyl phosphates.

2. The O/W-emulsion as claimed in claim 1, further comprising:
    0.1-10% by weight of a stabilizer; and/or
    1-10% by weight of a co-emulsifier;
    wherein the percentage by weight indicated relates to the total mass of the O/W-emulsion.

3. The O/W-emulsion as claimed in claim 1, further comprising:
    dispersed solids;
    and/or
    UV-A- and/or UV-B-filters;
    and/or
    an antioxidant;
    and/or
    perfume oils;
    and/or
    other inactive ingredients.

4. The O/W-emulsion as claimed in claim 1, comprising:
    1-15% by weight of the O/W-emulsifier, wherein the percentage by weight indicated relates to the total mass of the O/W-emulsion.

5. The O/W-emulsion as claimed in claim 4, further comprising:
    0.1-10% by weight of a stabilizer; and/or
    1-10% by weight of a co-emulsifier;
    wherein the percentage by weight indicated relates to the total mass of the O/W-emulsion.

6. The O/W-emulsion as claimed in claim 1, wherein the pH of the emulsion is between 3 and 11.

7. The O/W-emulsion as claimed in claim 2, wherein the pH of the emulsion is between 4 and 9.

8. The O/W-emulsion as claimed in claim 3, wherein the pH of the emulsion is between 4 and 9.

9. The O/W-emulsion as claimed in claim 4, wherein the pH of the emulsion is between 4 and 7.

10. The O/W-emulsion as claimed in claim 5, wherein the pH of the emulsion is between 4 and 7.

11. The O/W-emulsion as claimed in claim 2, further comprising:
    dispersed solids;
    and/or
    UV-A- and/or UV-B-filters;
    and/or
    an antioxidant;
    and/or
    perfume oils;
    and/or
    other inactive ingredients.

12. The O/W-emulsion as claimed in claim 1, wherein the O/W-emulsifier contains no polyethylene glycol (PEG) and/or no other glycol and/or no paraffin and/or no isoparaffin.

13. The O/W-emulsion as claimed in claim 1, wherein the O/W-emulsifier consists of:
   (a) 35-45% by weight of hardened palm oil glycerides;
   (b) 15-35% by weight of potassium cetyl phosphates;
   (c) 25-30% by weight of cetyl alcohol;
   (d) 5-10% by weight of potassium phosphates; and
   (e) 0-15% by weight of other substances;
      wherein the percentages by weight indicated relate to the total mass of the O/W-emulsifier.

14. The O/W-emulsion as claimed in claim 1, wherein component (b) of the O/W-emulsifier comprises potassium monocetyl phosphate and potassium dicetyl phosphate in a ratio by weight of between 10:1 and 2.5:1.

15. The O/W-emulsion as claimed in claim 1, wherein component (d) of the O/W-emulsifier comprises potassium hydrogen phosphate.

16. The O/W-emulsion as claimed in claim 1, wherein component (b) of the O/W-emulsifier comprises potassium monocetyl phosphate and potassium dicetyl phosphate-in a ratio by weight of between 6:1 and 3:1.

17. The O/W-emulsion as claimed in claim 15, wherein the potassium hydrogen phosphate is 4% by weight or higher, with respect to the total mass of the O/W-emulsifier.

18. A method for manufacturing an O/W-emulsion comprising:
   preparing an aqueous phase and an oil phase;
   preparing an O/W-emulsifier comprising:
      (a) 30-50% by weight of hardened palm oil glycerides;
      (b) 15-35% by weight of potassium cetyl phosphates;
      (c) 20-30% by weight of cetyl alcohol; and
      (d) 5-15% by weight of potassium phosphate;
         wherein the percentages by weight indicated relate to the total mass of the O/W-emulsifier;
   incorporating the emulsifier into the aqueous and/or the oil phase; and
   after incorporation of the emulsifier, mixing the aqueous phase with the oil phase until the O/W-emulsion has formed, and wherein the potassium phosphates of component (d) do not comprise cetyl phosphates.

* * * * *